US006702753B2

(12) United States Patent
Nunome

(10) Patent No.: US 6,702,753 B2
(45) Date of Patent: Mar. 9, 2004

(54) BLOOD PRESSURE MEASURING APPARATUS

(75) Inventor: Tomohiro Nunome, Komaki (JP)

(73) Assignee: Colin Corporation, Komaki (JP)

( * ) Notice: Subject to any disclaimer, the term of this patent is extended or adjusted under 35 U.S.C. 154(b) by 25 days.

(21) Appl. No.: 10/014,583

(22) Filed: Dec. 14, 2001

(65) Prior Publication Data

US 2002/0188208 A1 Dec. 12, 2002

(30) Foreign Application Priority Data

Jun. 6, 2001 (JP) ........................................ 2001-171492

(51) Int. Cl.[7] ................................................. A61B 5/02
(52) U.S. Cl. ........................................ 600/490; 600/485
(58) Field of Search ................................ 600/490, 485, 600/493–6

(56) References Cited

U.S. PATENT DOCUMENTS 5,161,538 A * 11/1992 Fukura et al. ............... 600/490
5,868,679 A * 2/1999 Miyazaki ..................... 600/494

FOREIGN PATENT DOCUMENTS

| DE | 19828588 A | 12/1999 | |
| EP | 0569308 A | 11/1993 | |
| EP | 1050266 A | 11/2000 | |
| EP | 1249218 A | 10/2002 | |
| WO | 00/00153 | * 1/2000 | ................. 606/202 |
| WO | WO 0072797 A | 12/2000 | |

* cited by examiner

Primary Examiner—Robert L. Nasser
(74) Attorney, Agent, or Firm—Oliff & Berridge, PLC

(57) ABSTRACT

An apparatus for measuring a blood pressure of a superior limb or an inferior limb of a living subject, including a blood-pressure measuring device which includes a measuring member adapted to be worn on a measurement portion of the superior or inferior limbs and measures a blood pressure of the measurement portion, and a pressing device which includes a pressing member adapted to be worn on the measurement portion or a distal portion of the subject relative to the measurement portion, and which presses the pressed portion with a prescribed blood-flow promoting force that is lower than a systolic blood pressure of the subject.

8 Claims, 3 Drawing Sheets

BLOOD PRESSURE MEASURING APPARATUS

BACKGROUND OF THE INVENTION

1. Field of the Invention

The present invention relates to a blood pressure measuring apparatus and particularly to the art of preventing or eliminating retention of venous blood and thereby improving accuracy of blood pressure measurement.

2. Related Art Statement

Before or after a surgical operation, a patient needs to rest on a bed without moving his or her superior or inferior limbs for a long time. If the patient does not move his or her superior or inferior limbs for a long time, then blood tends to stay in large venous sinuses that are present in muscles and are free of valves. Normally, the contractions of the muscles send the blood staying in the veins, back to the proximal side, i.e., the heart. In a special case, however, in which the patient's muscle forces are not so strong, the blood cannot flow so fast and accordingly tends to stay in the veins. In particular, blood is likely to stay in veins of legs.

If blood pressure values are measured from a portion of the patient in which venous blood stays, an accurate diastolic blood pressure cannot be measured. Since, however, a conventional blood pressure measuring apparatus measures blood pressure values without taking into account whether blood stays in veins, an accurate diastolic blood pressure may not be obtained.

SUMMARY OF THE INVENTION

It is therefore an object of the present invention to provide a blood pressure measuring apparatus which can measure an accurate blood pressure from a portion of a living subject that suffers retention of venous blood.

The above object has been achieved by the present invention. According to a first feature of the present invention, there is provided an apparatus for measuring a blood pressure of at least one of a superior limb and an inferior limb of a living subject, comprising a blood-pressure measuring device which includes a measuring member adapted to be worn on a measurement portion of said one of the superior and inferior limbs and measures a blood pressure of the measurement portion; and a pressing device which includes a pressing member adapted to be worn on a pressed portion of the subject that comprises at least one of the measurement portion and a distal portion of the subject relative to the measurement portion, and which presses the pressed portion with a prescribed blood-flow promoting force that is lower than a systolic blood pressure of the subject.

According to this invention, the pressing device presses the blood-pressure measurement portion of the subject or the distal portion of the subject relative to the measurement portion, and then stops pressing the measurement or distal portion. Consequently, flow of blood is promoted in veins of the measurement portion on which the measuring member is worn and a proximal portion of the subject relative to the measurement portion. Therefore, even if the measurement or proximal portion may suffer retention of venous blood, the retention can be eliminated. That is, since the pressing device presses the measurement or distal portion of the subject and then stops pressing the portion, the present apparatus can measure an accurate blood pressure of the subject.

According to a second feature of the present invention that includes the first feature, the pressing device further comprises pressing means for controlling, before the blood-pressure measuring device starts measuring the blood pressure of the measurement portion, the pressing member to first press the pressed portion with the blood-flow promoting force and then decrease the blood-flow promoting force.

The pressing means may control the pressing member such that immediately before the blood-pressure measuring device starts measuring the blood pressure of the measurement portion, the pressing member presses the pressed portion of the subject. Alternatively, the pressing means may control the pressing member such that before the blood-pressure measuring device starts measuring the blood pressure, the pressing member periodically presses the pressed portion of the subject at a prescribed period.

According to the first feature, the pressing device may be one which is manually operated to press the measurement portion of the subject. In this case, if an operator can judge that the measurement portion does not suffer retention of venous blood (e.g., because the subject is very young), an accurate blood pressure can be measured without having to operating the pressing device to press the measurement portion with the blood-flow promoting force. In this case, however, the pressing operation of the pressing device must be initiated by a different action of the operator than an action needed to initiate the blood-pressure measuring operation. Thus, the manually operable pressing device is less easy to use than the pressing device according to the second feature. In addition, the operator may erroneously initiate the blood pressure measuring operation without initiating the pressing operation of the manually operable pressing device, where the pressing operation is needed. In this case, an inaccurate blood pressure may be measured. In contrast, according to the second feature, the pressing means automatically eliminates retention of venous blood before commencement of the blood-pressure measuring operation. Thus, the present apparatus can be easily operated and can measure an accurate blood pressure of the subject.

According to a third feature of the present invention that includes the first or second feature, the measuring member of the blood-pressure measuring device comprises an inflatable cuff which is adapted to be worn on the measurement portion of the one of the superior and inferior limbs, and the pressing member of the pressing device comprises the inflatable cuff.

According to this feature, the cuff as part of the blood-pressure measuring device is used as part of the pressing device, and it is not needed to employ an exclusive pressing member in addition to the cuff.

BRIEF DESCRIPTION OF THE DRAWINGS

The above and optional objects, features, and advantages of the present invention will be better understood by reading the following detailed description of the preferred embodiments of the invention when considered in conjunction with the accompanying drawings, in which.

DETAILED DESCRIPTION OF PREFERRED EMBODIMENTS

Hereinafter, there will be described an embodiment of the present invention in detail by reference to the drawings. FIG.

1 is a diagrammatic view showing a construction of a blood pressure measuring apparatus 10 to which the present invention is applied.

Figure 1:
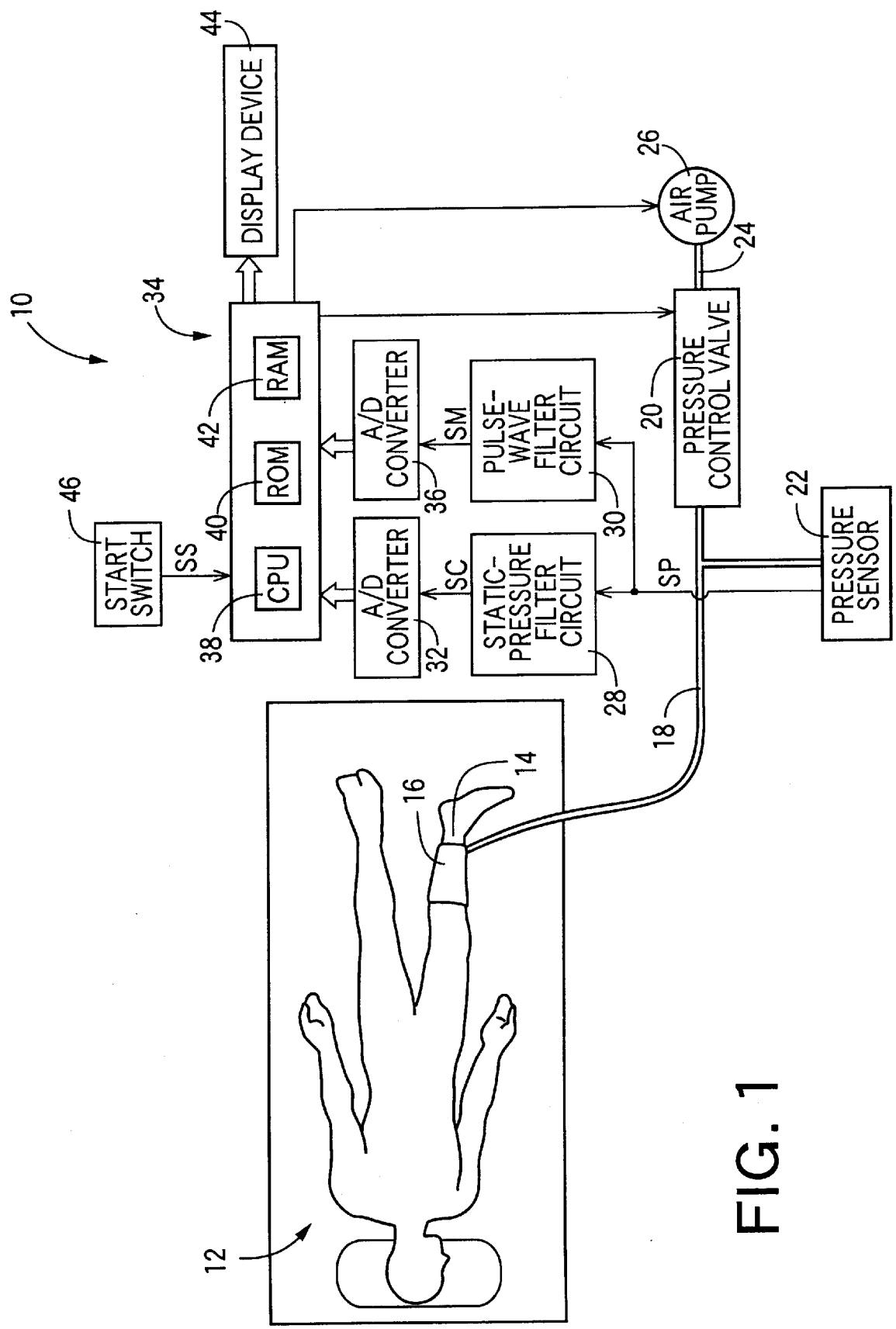
FIG. 1 is a diagrammatic view for explaining a construction of a blood pressure measuring apparatus to which the present invention is applied.

In FIG. 1, the blood pressure measuring apparatus 10 includes an inflatable cuff (i.e., a pressing band) 16 which is adapted to be wound around a leg 14 of a patient 12 who is taking a face-up position. The cuff 16 is a common leg cuff that includes a band-like outer bag formed of non-stretchable cloth or polyester and a rubber bag accommodated in the outer bag and has a width of, e.g., 18 cm. Although the present apparatus 10 is a blood pressure measuring apparatus of a type which measures a blood pressure of a living subject using the cuff 16, the cuff 16 also functions as a pressing device which presses a portion of the subject from which a blood pressure of the subject is to be measured, before the blood pressure is actually measured.

The cuff 16 is connected to a pressure control valve 20 and a pressure sensor 22 via a piping 18. The pressure control valve 20 is connected to an air pump 26 via a piping 24.

The pressure sensor 22 detects an air pressure in the cuff 16, and supplies a pressure signal SP representing the detected pressure, to each of a static-pressure filter circuit 28 and a pulse-wave filter circuit 30. The pressure control valve 20 is selectively placed in a pressure-supply position in which the control valve 20 permits a pressurized air to be supplied from the air pump 26 to the cuff 16, a pressure-keep position in which the control valve 20 keeps the air pressure in the cuff 16, a slow-deflation position in which the control valve 20 permits the pressurized air to be slowly discharged from the cuff 16, and a quick-deflation position in which the control valve 20 permits the pressurized air to be quickly discharged from the cuff 16.

The static-pressure filter circuit 28 includes a low-pass filter and extracts, from the pressure signal SP, a static-pressure component PC contained in the signal SP, i.e., a cuff-pressure signal SC representing the static pressure PC in the cuff 16. The cuff-pressure signal SC is supplied to a control device 34 via an A/D (analog-to-digital) converter 32. The pulse-wave filter circuit 30 includes a band-pass filter and extracts, from the pressure signal SP, an oscillating component having predetermined frequencies, i.e., a pulse-wave signal SM. The pulse-wave signal SM is supplied to the control device 34 via an A/D converter 36. The pulse-wave signal SM represents a pulse wave, i.e., a pressure wave that is produced from an artery of the patient in synchronism with the heartbeat of the patient and is propagated to the cuff 16.

The control device 34 is provided by a so-called microcomputer including a CPU (central processing unit) 38, a ROM (read only memory) 40, a RAM (random access memory) 42 and an I/O (input-and-output) port, not shown. The CPU 38 processes signals according to control programs pre-stored in the ROM 40 by utilizing a temporary-storage function of the RAM 42, and supplies control signals to the pressure control valve 20 and the air pump 26 through the I/O port. In addition, the CPU 38 determines, based on the cuff-pressure signal SC supplied from the static-pressure filter circuit 28 and the pulse-wave signal SM supplied from the pulse-wave filter circuit 30, a blood-pressure value BP of the patient, and operates a display device 44, to display the thus determined blood-pressure value BP.

The present apparatus 10 further includes a start switch 46 which supplies, each time it is operated by an operator, the control device 34 with a measurement-start signal SS that commands the control device 34 to start a blood-pressure measurement.

Figure 2:
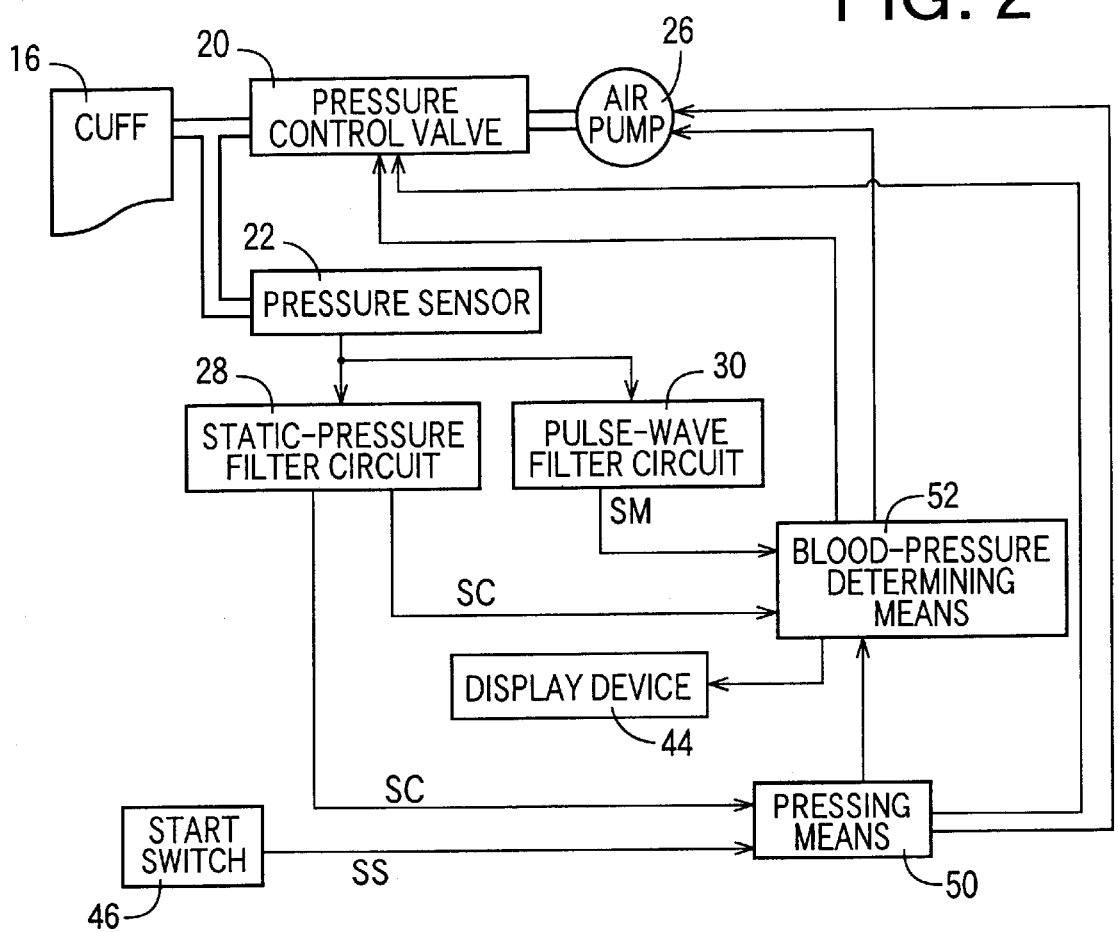
FIG. 2 is a block diagram for explaining essential functions of a control device of the apparatus of FIG. 1.

FIG. 2 is a block diagram for explaining essential functions of the control device 34. In the figure, a pressing means 50 carries out, when receiving the measurement-start signal SS from the start switch 46, a blood-flow promoting operation, as follows: Upon reception of the measurement-start signal SS, the pressing means 50 starts the air pump 26 and switches the pressure control valve 20 to its pressure-supply position, and thereby quickly increases, based on the cuff-pressure signal SC supplied from the static-pressure filter circuit 28, the pressure in the cuff 16 up to a prescribed blood-flow promoting pressure PP. Subsequently, the pressing means 50 stops the air pump 26 and switches the pressure control valve 20 to its quick-deflation position, and thereby quickly decreases the pressure of the cuff 16. The pressing means 50 repeats this pressure increasing and decreasing action a prescribed number N1 of times. The number N1 may be equal to one time or several times. The pressure increasing and decreasing action promotes flow of venous blood in the leg 14, thereby eliminating retention of the venous blood in the leg 14. The blood-flow promoting pressure PP may be prescribed at a pressure lower than a common or average systolic blood pressure of a human person, more preferably lower than a common or average diastolic blood pressure of a human person, and most preferably substantially equal to, or somewhat higher than, a common or average venous blood pressure of a human person. The promoting pressure PP may be equal to, e.g., 50 mmHg.

A blood-pressure (BP) determining means 52 is started after the pressing means 50 finishes the blood-flow promoting operation. The BP determining means 52 changes the cuff pressure PC by controlling the air pump 26 and the pressure control valve 20, and determines a BP value BP of the patient 12 based on the cuff-pressure signal SC and the pulse-wave signal SM which are obtained while the cuff pressure PC is changed. More specifically described, first, the BP determining means 52 controls the air pump 26 and the pressure control valve 20 to quickly increase the cuff pressure PC up to a prescribed target pressure PCM (e.g., 180 mmHg) and then slowly decrease the cuff pressure PC at a rate of, e.g., 3 mmHg/sec. Subsequently, the BP determining means 52 determines, based on the cuff-pressure signal SC continuously supplied from the static-pressure filter circuit 28 and the pulse-wave signal SM continuously supplied from the pulse-wave filter circuit 30 during the slow decreasing of the cuff pressure PC, a systolic BP value BP(SYS), a mean BP value BP(MEAN), and a diastolic BP value BP(DIA) of the leg 14 of the patient 12, according to well-known oscillometric method. After determining the diastolic BP value BP(DIA), the BP determining means 52 quickly deflates the cuff 16.

Figure 3:
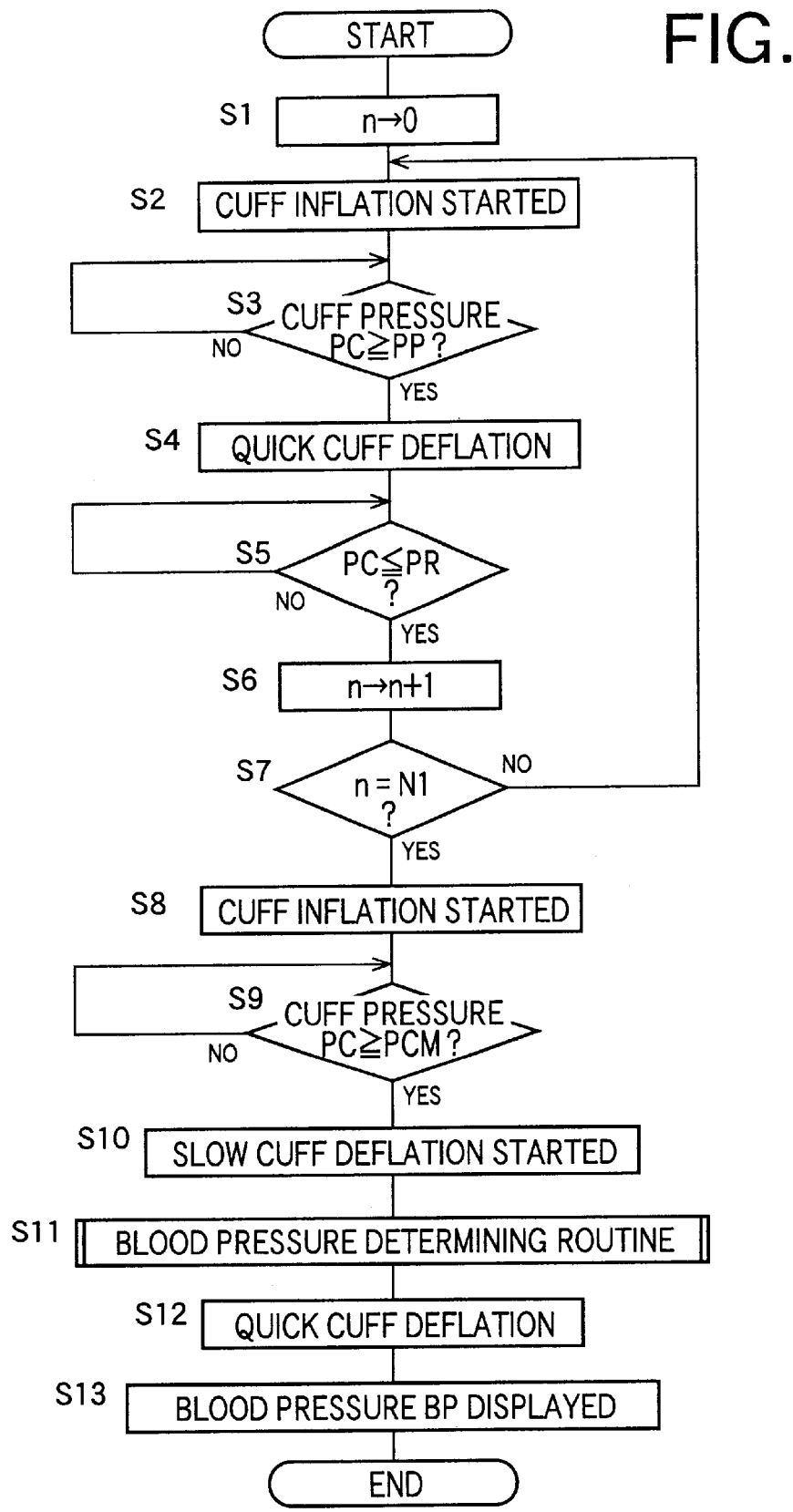
FIG. 3 is a flow chart representing a control routine according to which the control device of FIG. 2 operates.

FIG. 3 shows a flow chart representing a control routine according to which the control device 34 is operated.

The control routine represented by the flow chart of FIG. 3 is carried out when the start switch 46 is operated to supply the measurement-start signal SS to the control device 34. First, the control device carries out Steps S1 to S7 corresponding to the pressing means 50 (hereinafter, the term "Step(s)" is omitted, if appropriate).

At S1, the control device resets, to zero, a counter, n, that counts a prescribed number N1 of times by which a pressure increasing and decreasing action is repeated in a blood-flow promoting operation. Then, at S2, the control device switches the pressure control valve 20 to the pressure-supply position, and starts the air pump 26, so as to start quick increasing of the cuff pressure PC. Then, at S3, the control device judges whether the cuff pressure PC has been increased up to the blood-flow promoting pressure PP, e.g., 50 mmHg. If a negative judgment is made at S3, S3 is repeated while the increasing of the cuff pressure PC is continued.

Meanwhile, if a positive judgment is made at S3, the control goes to S4 to temporarily stop the air pump 26 and switch the pressure control valve 20 to the quick-deflation position, so that the pressure in the cuff 16 is decreased. Then, at S5, the control device judges whether the cuff pressure PC has been decreased down to a prescribed pressure-release pressure PR that is prescribed at a pressure equal to, or somewhat higher than, an atmospheric pressure. At the pressure-release pressure PR, the cuff 16 cannot press the leg 14 any longer. If a positive judgment is made at S5, S5 is repeated while the decreasing of the cuff pressure PC is continued.

Meanwhile, if a positive judgment is made at S5, the control goes to S6 to add one to the counter n, and then goes to S7 to judge whether the counter n indicates the prescribed number N1 of times, e.g., 3 times. If a negative judgment is made at S7, the control goes back to S2 and the following steps, to repeat the pressure increasing and decreasing action by the cuff 16 to promote the flow of blood in the leg 14.

If a positive judgment is made at S7, then the control goes to Step sS8 to S13 corresponding to the BP determining means 52.

First, at S8, the control device switches the pressure control valve 20 to the pressure-supply position, and starts the air pump 26, so as to start quick increasing of the cuff pressure PC. Then, at S9, the control device judges whether the cuff pressure PC has been increased up to a prescribed target pressure PCM, e.g., 180 mmHg. If a negative judgment is made at S9, S9 is repeated while the increasing of the cuff pressure PC is continued.

Meanwhile, if a positive judgment is made at S9, the control goes to S10 to switch the pressure control valve 20 to the slow-deflation position, so that the pressure in the cuff 16 is slowly decreased at the prescribed rate, e.g., 3 mmHg/sec.

Then, at S11, a BP determining routine is carried out. More specifically described, the control device determines an amplitude of each of heartbeat-synchronous pulses of the pulse wave represented by the pulse-wave signal SM continuously supplied from the pulse-wave filter circuit 30 and determines, based on the change of the thus determined amplitudes, a systolic BP value BP(SYS), a mean BP value BP(MEAN), and a diastolic BP value BP(DIA) of the patient 12 according to a well-known oscillometric BP determining algorithm.

After the diastolic BP value BP(DIA) is determined at S11, the control goes to S12 to switch the pressure control valve 20 to the quick-deflation position and stop the air pump 26. Then, at Step S13, the control device operates the display device 44 to display the thus determined BP values BP(SYS), etc.

It emerges from the foregoing description of the embodiment that employs the flow chart shown in FIG. 3, that before a blood-pressure measurement is started, the cuff 16 is inflated to press, with the blood-flow promoting pressure PP, a portion of the patient 12 from which a blood pressure is to be measured, and then the cuff 16 is deflated to stop pressing that portion. If the cuff 16 presses the portion (i.e., the leg 14) from which blood pressure is to be measured, and then stops pressing the portion, flow of blood is promoted in veins of the portion or a proximal-side portion of the patient 12 that is located on a proximal side of the portion. Thus, retention of blood in those veins, if any, is eliminated. Therefore, the present apparatus 10 can measure an accurate blood-pressure value BP of the patient 12.

In addition, in the illustrated embodiment employing the flow chart of FIG. 3, at Steps S1 to S7 (the pressing means 50), the control device 34 automatically operates, before a blood-pressure measurement is started, the cuff 16 to eliminate retention of venous blood. Thus, the present apparatus 10 can be easily used to obtain a reliable and accurate BP value BP of the patient 12.

Moreover, in the illustrated blood pressure measuring apparatus 10, the cuff 16 is used for carrying out not only the blood pressure measurement but also the blood-flow promoting operation. Thus, it is not needed to employ an exclusive pressing device to press a portion of the patient 12 from which a blood pressure is to be measured.

While the present invention has been described in its preferred embodiment, the present invention may be otherwise embodied.

For example, in the blood pressure measuring apparatus 10 shown in FIG. 1, the blood-pressure values BP are measured from the leg 14 of the patient 12. However, it is possible to adapt the apparatus 10 to measure one or more blood-pressure values from one or two superior limbs (e.g., upper arm or arms) and/or one or two inferior limbs (e.g., femoral portion or portions) of the patient 12. In addition, in the blood pressure measuring apparatus 10 shown in FIG. 1, the BP determining means 52 is designed to determine a BP value according to the oscillometric method. However, the BP determining means may be designed to determine a BP value according to so-called Korotkoff-sound method in which a cuff pressure at the time when the first one of Korotkoff sounds is detected is determined as a systolic BP value and a cuff pressure at the time when the last Korotkoff sound is detected is determined as a diastolic BP value. Otherwise, the BP determining means may be one which employs, for measuring blood pressure, a supersonic Doppler method in which a supersonic generator placed right above an artery generates a supersonic signal when a pressing force applied to the artery is changed, and a receiver receives the supersonic signal to detect opening and closing of the artery.

In addition, the blood pressure measuring apparatus 10 shown in FIG. 1 employs the single pressing device (the cuff 16). However, it is possible to employ two or more pressing devices, e.g., two pressing devices that are adapted to be worn on upper and lower sides of a calf of the leg 14, respectively. In the latter case, the pressing devices are controlled to sequentially press a portion of the patient 12, in an order starting with the most downstream one of the pressing devices as viewed in the direction of flow of arterial blood.

In the blood pressure measuring apparatus 10, the cuff 16 for use in blood pressure measurement is also used as the pressing device. However, it is possible to employ an exclusive pressing device that is independent of the blood-pressure-measurement cuff 16. In the latter case, the pressing device is worn on a distal portion of the patient 12 that is continuous with a proximal portion of the patient 12 from which blood pressure is to be measured. For example, in the case where blood pressure is measured from a femoral portion of a living subject, the pressing device is worn on a distal portion of the leg including the femoral portion.

In the blood pressure measuring apparatus 10, the cuff 16 for use in blood pressure measurement is also used as the pressing device which presses, with the blood-flow promoting pressure PP, a portion of the patient 12 from which blood pressure is to be measured, before the blood pressure is actually measured. However, it is possible to press, with the blood-flow promoting pressure PP, a distal portion of the patient 12 that is continuous with the portion of the patient 12 from which blood pressure is to be measured. That is, the cuff 16 may be used in such a manner that first the cuff 16 is worn on a distal portion of the patient 12 relative to a portion of the patient 12 from which blood pressure is to be measured and is used to press the distal portion with the blood-flow promoting pressure PP and then the cuff 16 is re-worn on the portion of the patient 12 from which blood pressure is to be measured.

In addition, in the blood pressure measuring apparatus 10, when the start switch 46 is operated, the cuff 16 is used to press the leg 14 with the blood-flow promoting pressure PP and subsequently is used to measure a blood-pressure value BP of the patient 12. However, the apparatus 10 may employ two different switches that are operated to command a blood pressure measuring operation and a blood-flow promoting operation, respectively.

It is to be understood that the present invention may be embodied with other changes, improvements, and modifications that may occur to a person skilled in the art without departing from the spirit and scope of the invention defined in the appended claims.

What is claimed is:

1. An apparatus for measuring a blood pressure of at least one of a superior limb and an inferior limb of a living subject, comprising:

a blood-pressure measuring device which includes a measuring member adapted to be worn on a measurement portion of said one of the superior and inferior limbs and measures a blood pressure of the measurement portion; and a pressing device which includes a pressing member adapted to be worn on a pressed portion of the subject that comprises at least one of the measurement portion and a distal portion of the subject relative to the measurement portion, and which presses the pressed portion with a prescribed blood-flow promoting force that is lower than a systolic blood pressure of the subject, wherein the pressing device further comprises pressing means for controlling, before the blood-pressure measuring device starts measuring the blood pressure of the measurement portion, the pressing member to first press the pressed portion with the blood-flow promoting force and then decrease the blood-flow promoting force, and wherein the pressing means comprises repeating means for repetitively controlling, before the blood-pressure measuring device starts the blood pressure measurement, the pressing member to first press the pressed portion with the blood-flow promoting force and then decrease the blood-flow promoting force.

2. An apparatus according to claim 1, wherein the repeating means repetitively controls, a prescribed number of times, the pressing member to first press the pressed portion with the blood-flow promoting force and the decrease the blood-flow promoting force.

3. An apparatus according to claim 1, wherein the measuring member of the blood-pressure measuring device comprises an inflatable cuff which is adapted to be worn on the measurement portion of said one of the superior and inferior limbs, and wherein the pressing member of the pressing device comprises the inflatable cuff.

4. An apparatus according to claim 1, wherein the prescribed blood-flow force is lower than a diastolic blood pressure of the subject.

5. An apparatus according to claim 1, wherein the prescribed blood-flow promoting force is around a venous blood pressure of the subject.

6. An apparatus according to claim 1, wherein the prescribed blood-flow promoting force is equal to 50 mmHg.

7. An apparatus according to claim 3, wherein the blood-pressure measuring device additionally comprises:

a pressure sensor which detects a pressure in the cuff;

a pressure changing device which changes the pressure in the cuff a pulse-wave sensor which detects a pulse wave occurring to the cuff while the pressure of the cuff is changed by the pressure changing device; and means for determining the blood pressure of the measurement portion based on the pulse wave detected by the pulse-wave sensor.

8. An apparatus according to claim 1, further comprising a display device which displays the blood pressure measured by the blood-pressure measuring device.

* * * * *